United States Patent [19]

Larson et al.

[11] 4,374,127
[45] Feb. 15, 1983

[54] HERPES SUB UNIT VACCINE

[75] Inventors: Vivian M. Larson, Harleysville; E. Dale Lehman, Lansdale, both of Pa.

[73] Assignee: Merck & Co., Inc., Rahway, N.J.

[21] Appl. No.: 120,409

[22] Filed: Feb. 11, 1980

Related U.S. Application Data

[63] Continuation-in-part of Ser. No. 934,554, Aug. 21, 1978, abandoned, which is a continuation-in-part of Ser. No. 834,598, Sep. 19, 1977, abandoned.

[51] Int. Cl.$^3$ ............................................. A61K 39/245
[52] U.S. Cl. ........................................ 424/89; 435/235
[58] Field of Search ................... 424/89; 435/235, 239

[56] References Cited

U.S. PATENT DOCUMENTS

| | | | |
|---|---|---|---|
| 3,452,135 | 6/1969 | Medveczky | 424/9 |
| 3,651,213 | 3/1972 | Wallis et al. | 424/89 |
| 3,897,549 | 7/1975 | Zygraich et al. | 424/89 |
| 3,897,549 | 7/1975 | Zygraich et al. | 424/89 |
| 4,140,762 | 2/1979 | Bachmayor et al. | 424/89 |
| 4,235,877 | 11/1980 | Fullerton | 424/89 |

FOREIGN PATENT DOCUMENTS

| | | | |
|---|---|---|---|
| 1365 | 4/1979 | European Pat. Off. | 424/89 |
| 2300M | 1/1964 | France | 424/89 |
| 1140316 | 1/1969 | United Kingdom | 424/89 |

OTHER PUBLICATIONS

Perlant Chem. Abstr. 83 #103267k (1975) of Ger. Offen. 2,454,870 28 May 1975.
Asulai et al. Chem. Abstr. 86 #195230f (1977) of U.S. 4,020,183 26 Apr. 1977.
Spear et al., J. Virol., No. 9, Jan. 1972, pp. 143–159.
C.A. 89:204,040k, 1978.
J. Virol., Jan. 1972, pp. 143–159.
New Trends Dev. Vaccines 1978, 179–210, Voller et al., Univ. Park Press, Baltimore, Md.
Acta Virol., May 1980, vol. 24, No. 3, pp. 183–193.
Arch. Virol., 1980, vol. 65, No. 1, pp. 15–23.
C.A. 81:167,577c, 1974.
C.A. 82:7,637q, 1975.
C.A. 83:103,267k, 1975.
C.A. 86:195,230f, 1977.
C.A. 88:72,916t, 1978.
C.A. 89:54,017s, 1978.
C.A. 67:62,606u, 1967.
C.A. 75:16,540k, 1971.
C.A. 77:59,963j, 1972.
C.A. 77:73,599b, 1972.
C.A. 79:108,051n, 1973.
C.A. 80:19,527a, 1974.
Vernon et al., Chem. Abstracts 89:204040k (1978) of New Trends Dev. Vacines (1978):179–210.
Tokumeru et al., Chem. Abstracts 73:23465b (1970) of Arch. Gesamte. Virusf. 197029(4):295–306.
Becker et al., Chem. Abstracts 75:16540k (1971) of Isr. J. Med. Sci. (1971) 7(5):656–662.
Ponce de Leon et al., Chem. Abstracts 79:124495r (1973) of J. Virol. (1973) 12(4):766–774.
Savage et al., Chem. Abstracts 78:13591d (1973) of J. Gen. Virol. (1972), Pt. 1:31–48.
Gibson et al., Chem. Abstracts 78:25678a (1973) of J. Virol. (1972) 10(5):1044–1052.
Skinner G. et al., Med. Microbiol. Immunol. 166 (1–4):117–132 (1978) Preparation and Efficacy of an Inactivated Subunit Vaccine Against Type 2 Herpes Simplex Virus Infection.
Cappel R. et al., Abstr. Annu. Meet. Am. Soc. Microbiol. 78(1978):263 Antibody and Cell-Mediated Immunity to a Herpes Simplex Type 2 Virus Subunit Vaccine.
Klein H. D. et al., Theor. Appl. Genet. 48(5):227–235 (1976) Immunization with Live, u/v Inactivated Herpes Simplex Virus and a Subunit Vaccine and Efficacy of these Immunizations.
Cappel R. et al., Dev. Biol. Standards 43:381–385 (1979) Antibody and Cell-Mediated Immunity to a DNA--Free Herpes Simplex Sub-Unit Vaccine.
Cappel R. et al., Arch. Virol (1980) 65(1):15–23 Efficacy of a Nucleic Acid Free Subunit Vaccine.
Strnad et al., Chem. Abstr. 84 #147378x (1976) of Virology 1976 69(2):438–452.
Colbere Chem. Abstr. 83 #128475q (1975) of Bull. Inst. Pabtuer, Paris (1975) 73(3):203–254.
Avrelian Chem. Abstr. 86 #69826s (1977) of Tumor Virus Infect. Immun. Proc. Symp. (1975) 89–131.

Primary Examiner—Shep K. Rose
Attorney, Agent, or Firm—Donald J. Perrella; Hesna J. Pfeiffer

[57] ABSTRACT

Herpes virus subunit antigens suitable for vaccine use are prepared by (1) treating virus-infected cells with a surfactant and varying concentrations of salt to extract and solubilize viral-directed glycoproteins, (2) fractionating the solubilized material by chromatographic procedures to enrich the viral-directed glycoproteins and to remove unwanted proteins and nucleic acids, and (3) optionally treating the subunit antigens with deoxyribonuclease and formaldehyde to assure safety.

8 Claims, 4 Drawing Figures

HERPES SUB UNIT VACCINE

The Government has rights in this invention pursuant to Contract NIH-NCI-71-2059 awarded by the Department of Health, Education and Welfare.

RELATED APPLICATION

This application is a continuation-in-part of our copending application Ser. No. 934,554 filed Aug. 21, 1978, now abandoned which in turn is a continuation-in-part of application Ser. No. 834,598, filed Sept. 19, 1977, now abandoned.

BACKGROUND OF THE INVENTION

1. Field of the Invention

This invention relates to the preparation of herpesvirus subunit vaccines, and in particular to *Herpes simplex* type 1 and 2 vaccines.

Herpesviruses are ubiquitous in nature; natural hosts include the frog, chicken, mouse, quinea pig, cat, dog, swine, cow, horse, monkey and man. Man is the natural host for *Herpes simplex* type 1 and 2, varicella/zoster, cytomegalovirus and Epstein-Barr virus (EBV) and can be a temporary host for herpes B virus of monkeys with serious consequences. Clinical illness caused by herpes viruses presents a significant health problem for which no effective preventive measures are available. *Herpes simplex* type 1 and 2 are antigenically related, but generally cause infections at different sites. *Herpes simplex* type 1 (HSV1) is transmited by the oral-respiratory route and is most frequently associated with oral lesions. *Herpes simplex* type 2 (HSV2) is transmitted venereally and is usually responsible for herpes genitalis and neonatal herpes. The role of these virus in chronic disease has not been defined. However, HSV2 has been implicated in genital cancer on the basis of: (a) sero-epidemiologic findings, (b) demonstration of herpesvirus antigens or viral nucleic acid in neoplastic tissue, and (c) in vitro transformation of a variety of cells, including human cells, by irradiated virus.

Members of the herpesvirus group are relatively large enveloped ether-sensitive DNA viruses. *Herpes simplex* type 1 viruses have been shown characteristically to contain two predominant molecular weight groups of envelope glycoproteins whereas type 2 viruses have been shown characteristically to possess three predominant molecular weight groups of envelope glycoproteins. Some of these glycoproteins have been isolated and shown to induce neutralizing antibody in animals.

Herpesviruses present unique and individual problems for vaccine development, especially for use in man. Generally, viral vaccines, whether live attenuated vaccines or killed inactivated vaccines, are prepared from virus contained in animal host fluids or cell culture fluids or viral concentrates derived therefrom. However, herpesviruses in general tend to be more cell-associated than many other viruses, i.e., do not shed into the fluids, and, especially some members of the group, do not propagate readily to the high level of virions required for large scale manufacture of vaccine. Additionally, certain herpesviruses, such as HSV2 and EBV, are suspected of being oncogenic for men. Preparation of vaccines from such viruses presents a special problem in that the vaccine must be free of any viral genetic information capable of inducing cancer. Even inactivated whole virus vaccines are viewed as potentially hazardous in such cases because they contain viral nucleic acid. Recently, efforts toward improved viral vaccines have lead to the development of subunit or "split" vaccines to reduce or remove unwanted host or viral components in the vaccines. An example in point is the preparation of influenza viral subunit vaccine from infected chick egg allantoic fluid to reduce the toxicity and pyrogenicity as described in U.S. Pat. No. 3,962,421. However, such subunit vaccines have not emphasized or demonstrated the removal and/or deactivation of viral genetic information as will be needed for viruses suspected of playing an etiologic role in cancer.

2. Objects of the Invention

It is an object of the present invention to provide a subunit antigen for a herpes virus. Another object is to provide an immunogenic but nonpathogenic herpes subunit antigen. A further object is to provide a herpes subunit antigen which can be used as a vaccine which protects a subject against the effects of this virus on both initial and subsequent challenge. Yet another object is to provide a method for effectively solubilizing and extracting viral-directed glycoproteins from virus-infected cells utilizing a surfactant and salt. Another object is to provide a method for concentrating the glycoproteins and removing unwanted protein and nucleic acid. Another object is to provide compositions containing a herpes subunit which are stable and storable. Still another object is to provide physiologically acceptable compositions for administering a herpes subunit vaccine. These and other objects of the present invention will be apparent from the following description.

SUMMARY OF THE INVENTION

Primary chick embryo cells infected with HSV1 or HSV2 are prepared and subjected to the following sequence of operations to extract and concentrate the viral-directed glycoproteins, separate them from unwanted materials and treat them to assure safety when used as a vaccine:

(1) the infected cells are treated with a surfactant, and a salt.
(2) the surfactant solubilized material is fractionated by DEAE-cellulose or lectin chromatography.
(3) the viral glycoprotein containing fraction optionally is treated by Sephadex G-50 chromatography, with deoxyribonuclease and with formaldehyde.

The resulting products are useful as HSV1 and HSV2 vaccines. The general process is applicable to other members of the herpesvirus group when the viruses are propagated in the host cell system appropriate for the particular herpesvirus.

DETAILED DESCRIPTION

According to the present invention the starting material is herpesvirus infected cells propagated in cell culture. The virus may be any member of the herpesvirus group such as HSV1, HSV2, varicella/zoster, cytomegalovirus, EBV, simian B virus and the like. The cell may be any cell capable of being infected with the particular herpesvirus and of producing the desired viral antigens and considered acceptable for the preparation of a vaccine. For HSV1 and HSV2 vaccines for man, for example, a suitable cell culture system is primary chick embryo cells propagated as monolayers in roller bottles by procedures commonly used by those skilled in the art. The cells are infected with the HSV1 or HSV2 viruses at a low multiplicity of infection (MOI, i.e., the number of virus particles per cell), such as an MOI of from about 0.001 to about 1.0, preferably about 0.01, by techniques commonly used by those skilled in the art and the cultures are incubated until viral cytopathogenic effect is observed in a large proportion of the cells, typically about 75% of the cells. At the end of the incubation period, the cell culture medium is removed and the cell monolayer is optionally washed with a balanced salt solution. Alternately, the cells may be collected from the culture vessel by mechanical means, washed with a balanced salt solution, disrupted by procedures such as sonication, and the resulting disrupted cell suspension clarified by low speed centrifugation or the like. The instant method for solubilizing and extracting viral-directed membrane-bound glycoproteins from virus-infected cells can be applied as effectively to the above described intact cells in monolayers as to the disrupted cell extracts. Direct chemical extraction of the intact monolayer cell cultures offers a significant practical advantage for large scale vaccine manufacture as it does not require mechanical removal of the cells from the cell growth surface. It has also been found to give a higher protein yield by reducing physical losses involved in mechanical harvesting of cells and it permits elimination of the sonication step and the low speed centrifugation step. Under properly controlled conditions this procedure improves antigen purity by selective extraction of antigens, that is to say, less DNA is extracted compared to the mechanical harvesting and sonication procedure.

The surfactant employed for extraction may belong to the nonionic or anionic category. The nonionic surfactant employed may be, for instance, one or more of the following types:

1. Aryl ether adducts of ethylene oxide such as polyoxyethylene alkyl phenols. Specific examples of this type are polyoxyethylene octyl phenol (Triton X-100, Rohm & Haas, Nonidet P-40, Shell; Beloid EMP, Geigy), polyoxyethylene 9–9.5 nonyl phenol (Renex 698, Atlas), polyoxyethylene 9–10 nonyl phenol (Triton N101, Rohm & Haas) and polyoxyethylene 10.5 nonyl phenol (Tergitol NPX, Union Carbide).

2. Aliphatic ether adducts of ethylene oxide, such as polyoxyethylene aliphatic alcohols. Specific examples of this type are polyoxyethylene 10 oleyl alcohol (Brij 96, Atlas), polyoxyethylene 7 trimethylene 7 linear alcohol $C_{11}$–$C_{15}$ (Tergitol 15-S-7, Union Carbide).

3. Ester adducts of ethylene oxide, such as polyoxyethylene fatty acids. A specific example of this type is polyethylene glycol 400 monolaurate (Cithrol 4ML 400, Croda).

4. Amine adducts of ethylene oxide, such as, polyoxyethylene fatty amines. Specific examples of this type are polyoxyethylene 15 stearyl amine (Ethomeen 18/25, Armour), polyoxyethylene 15 coco fatty amines, average molecular weight 860 (Ethomeen C/25, Armour) and polyoxyethylene 5 soya fatty amines (Ethomeen S/15, Armour).

The anionic surfactant employed for extraction may be a bile salt such as, for example: sodium deoxycholate, sodium cholate or sodium taurocholate.

For extraction, a preferred type of nonionic surfactant is a polyoxyethylene alkyl phenol wherein the alkyl group has from about 6 to about 12 carbons, e.g. Triton X-100 or Nonidet P-40. Treatment with the nonionic surfactant extracts viral glycoproteins while treatment with the nonionc surfactant optionally in the presence of salt, typically from about 0.1 M up to about 2 M salt depending upon the virus, enhances extraction of viral glycoproteins. The salt may be an alkali salt, an alkaline earth salt or a salt of a trivalent cation. Examples of such salts are KCl, NaCl, $NH_4Cl$, $MgCl_2$ or $CaCl_2$. The extraction preferably takes place at neutral pH and a buffer, e.g. Tris-HCl, may be employed to adjust pH if necessary. A proteolytic inhibitor, e.g. phenyl methyl sulfonyl fluoride (PMSF), is optionally present. The extraction may take place at refrigerator temperature up to incubator temperature, i.e. from about 4° to about 37° C. for a period of from about 15 minutes to several days. The extraction period may extend up to that time at which degradation of the desired antigenic material occurs. However, there is generally no advantage to an extracted period of more than a few hours. Typically, the extraction is carried out in 2% Triton X-100, 0.15 M to 1 M NaCl, 10 mM Tris-HCl, pH 7.5, and 2 mM PMSF at 20°–23° C. for 1 to 4 hours.

Following extraction, the extract medium is centrifuged to remove insolubles: cell debris, cell nuclei and viral nucleocapsids. The centrifugation may be carried out at from about 50,000×g or above for from about 15 minutes to several hours, typically at about 100,000×g for about 1 hour. The soluble extract is non-infectious but contains some residual intact (double stranded) DNA and RNA. Double stranded (native) DNA and RNA are measured by the ethidium bromide assay of Karsten et al., *Anal. Biochem.*, 46, 135–148, 1972. The assay detects DNA in amounts as low as 50 ng and RNA in amounts as low as 100 ng. Total DNA (single and double stranded DNA, and DNA fragments) is measured by the method of Kissane et al., *J. Biol. Chem.*, 233, 184–188, 1958, which detects amounts as low as 50 ng.

Optionally the soluble material resulting from the extraction may be treated at this stage or subsequently during the process with DNase to hydrolyze any residual DNA and yield a product substantially free of intact (double stranded) DNA (less than 50 ng/100 μg protein).

The soluble material resulting from the extraction procedure with the nonionic surfactant is especially suitable as starting material for chromatographic purification of membrane-bound herpesvirus glycoproteins. Chromatographic fractionation in the presence of the surfactant results in enrichment of the viral glycoproteins, removal and/or reduction of DNA fragments, RNA and other undesirable proteins. Fractionation of the soluble material may be effected by anion-exchange chromatography by methods known to those skilled in the art. The anion exchange medium may be, e.g., DEAE-cellulose. If the DNase digestion is omitted, the product of DEAE-cellulose chromatography is substantially free of double stranded DNA (<50 ng/100 μg protein) but may contain residual total DNA (1 μg/100 μg protein). If DNase digestion is carried out before chromatography the product is substantially free of all DNA (<50 ng/100 μg protein). More preferably the soluble material may be fractionated by affinity chromatography on an immobilized lectin by procedures know to those skilled in the art. Lectins are cell-agglutinating proteins which occur most commonly in seeds of leguminous plants, but they are also found in other parts of the plants, in plants other than legumes, and in animals. Lectins cause agglutination by binding to carbohydrates on cell surfaces and it is this specificity which makes lectins useful in the isolation and purification of carbohydrate-containing macromolecules, such as glycoproteins. In their utility as glycoprotein purification reagents the lectins are usually insolubilized and immobilized by being covalently bound to an inert matrix such as, for example, dextrans, agarose, cellulose, and the like. Preferably the lectin is immobilized on a column.

Specific lectins are, for example, *Lens culinaris* lectin, Concanavalin A (*Canavalia enisformis* lectin), Soybean agglutinin (*Glycine max* lectin), Wheat germ agglutinin, Horse gram lectin (*Dolichos biflorus* lectin), *Lotus tetragonolobus* lectin *Phaselous lunatus* lectin (lima bean lectin), *Phaselous vulgaris* lectin (kidney bean lectin), Peanut lectin, *Pisum sativum* lectin (garden pea lectin), *Vicia graminea* lectin, *Robinia pseudoacacia* lectin (black locust lectin), *Vicia faba* lectin, *Ulex europeus* lectin (gorse lectin), *Vicia cracca* lectin, *Solanium tuberosum* lectin (potato lectin), *Abrus precatorius* lectin, *Triticum vulgaris* lectin (wheat lectin), *Momordia charantia* lectin, *Agaricus campestris* lectin (meadow mushroom lectin), *Sesanum indicum* lectin, Helix pomatia lectin (vineyard snail lectin), *Wisteria floribunda* lectin, *Laburnum alpinum* lectin, *Sophora japonica* lectin, *Phaseolus limensis* lectin, and *Limulus polyphemus* lectin, (horseshoe crab lectin). For HSV2 a preferred lectin is *Lens culinaris*, and for HSV1 a preferred lectin is concanavalin A. The product obtained from lectin affinity chromatography is substantially free of both double-stranded and total DNA (<50 ng/100 μg protein) even without DNase treatment and contains no detectable RNA (<100 ng/100 μg protein).

Optionally the viral subunit isolated by adsorption on the immobilized lectin may be treated with a material capable of adsorbing lectins which may have bled from the adsorbant. Such material may be a polymerized dextran, such as one of the Sephadex gels.

The viral directed glyoproteins isolated by either ion-exchange or affinity chromatography optionally can be further purified and separated by adsorption onto the calcium phosphate containing absorbents, e.g., brushite ($CaHPO_4.2H_2O$) or, more preferably, hydroxylapatite [$(Ca_{10}(PO_4)_6(OH)_2$]. Adsorption chromatography is performed in the presence of a surfactant by procedures known to those skilled in the art.

The viral subunit antigen resulting from treatment with either the anion-exchange resin or the immobilized lectin is free of detectable double stranded DNA and can be utilized as a vaccine to induce neutralizing antibody and cell-mediated immune responses and to protect laboratory animals against paralysis and death caused by the herpes virus. The viral subunit isolated by lectin adsorption contains no detectable DNA or RNA as determined by the foregoing assays while the viral subunit isolated by adsorption onto anion-exchange medium contains about 1.0% total DNA fragments or RNA.

The viral subunit vaccine may be sterile filtered and optionally treated with inactivating means such as, for example, heat, UV, DNase, formalin or thimerosal to insure safety. The immunizing effect of the viral subunit vaccine may be potentiated by adsorbing the viral subunit antigen on alum or by utilizing other immunologic adjuvants. For use as a vaccine, the viral subunit antigens must be substantially free of surfactant. The adsorption of the antigen to alum provides a particularly convenient means for removal of any unbound residual surfactant.

The present invention is applicable to any herpes family virus, such as, for example, herpes simplex type 1, herpes simplex type 2, EBV virus, cytomegalovirus, varicella/zoster and simian B virus.

The immunogenic antigens of the present invention may be prepared for vaccine use by combining with a physiologically acceptable composition such as, e.g. PBS, saline or distilled water and sterile filtering. The immunogenic antigens are administered in a dosage range of from about 1 to about 100 μg, preferably about 5 to about 50 μg, in order to obtain the desired immunogenic effect. The antigens may be administered in a single dose or in a series of doses at intervals of several weeks or months followed, if necessary, by a booster dose at an interval of several months to several years. An antimicrobial preservative, e.g. thimerosal, optionally may be present. Likewise, an inactivating agent, e.g., formaldehyde may be employed to kill any residual live virus, and to inactivate any single stranded nucleic acid.

The immunogenic antigens of the present invention may be employed, if desired, in combination with vaccine stabilizers and vaccine adjuvants. Typical stabilizers are, for example, gelatin, casein and albumin. An example of an adjuvant is alum. An adjuvant formulation may be prepared from peanut oil, isomannide monooleate and aluminum monostearate. The vaccine of the present invention may be stored under refrigeration or in frozen or lyophilized form. These antigens are immunogenic in mammalian species and are useful as vaccines based on induction of antibodies in guinea pigs, marmoset and Cebus monkeys, cats, and based on protection against lethal homologous virus infection in mice.

The following examples illustrate the present invention without, however, limiting the same thereto.

EXAMPLE 1

The Curtis strain of HSV2 was received from Dr. A. J. Nahmias of Emory University, Atlanta, Ga., with a passage history of 3 passages in primary rabbit kidney. This virus was passed 3 more times in rabbit kidney cells and then adapted to chick embryo cells by 8 serial passages.

Chick embryos from 11 day embryonated eggs from a leucosis-free flock are trypsinized and the resulting single cell suspension is planted in roller bottles in medium 199 containing 2% fetal calf serum and 50 μg/ml neomycin and incubated at 36° C. on a roller mill.

On day 4 the monolayer cultures are infected with the HSV 2 virus at an MOI of 0.01 with an initial adsorption period of 2 hours. The infected cultures are incubated at 34° C. on roller mills until cytopathic effect is observed in about 75% of the cells, at about 44–48 hours.

The supernatant growth medium is discarded and the monolayer cultures are washed gently (3×50 ml) with PBS while rotating on the roller mill to remove residual fetal calf serum. After the washing, an extractive medium containing 2% Triton X-100, 1 M NaCl, 50 mM Tris-HCl, pH 7.5, 2 mM PMSF, and 4.75% ethanol is added to the bottles while rotating on the mill at a temperature of 20°–23° C. and the extraction is allowed to proceed for about 30 minutes. The extracting medium is collected, the vessels are washed with additional extracting medium, and the wash fluid is added to the original extracting medium. The pooled cell extract is kept at a temperature of 20°–23° C. for a total time period of no less than 1 hour from the time of the first addition of extracting medium to the cell culture bottles and then centrifuged at 105,000 g for 1 hour at 20°–23° C.

The supernatant is adjusted to pH 7.0, $MgCl_2$ is added to a final concentration of 0.005 M, and deoxyribonuclease from bovine pancreas (1 mg/ml in deionized, distilled water) is added to give a final concentration of 50 μg/ml. The mixture is incubated at 20°–23° C. for 4 hours. This mixture is now substantially free of intact (double stranded) DNA.

The mixture is fractionated on a *Lens culinaris* lectin affinity column. The *Lens culinaris* lectin-Sepharose affinity adsorbent is prepared by covalently linking *Lens culinaris* lectin to CNBr-activated Sepharose 4B or activated CH-Sepharose 4B by known procedures. The adsorbent is suspended in 0.1% Triton X-100, 1.0 M NaCl, 50 mM Tris-HCl, pH 7.5 (starting buffer) and poured into a chromatography column; the final dimensions of the adsorbent bed are 2.6 cm (inside diameter)×10 cm (53.1 ml bed volume). The adsorbent is washed with 250 ml of 0.2 M α-methyl-D-mannoside in starting buffer and this is followed by at least 5 column volumes of starting buffer. Flow rate of the column is maintained at 100 ml/hr with a peristaltic pump.

Figure 1:
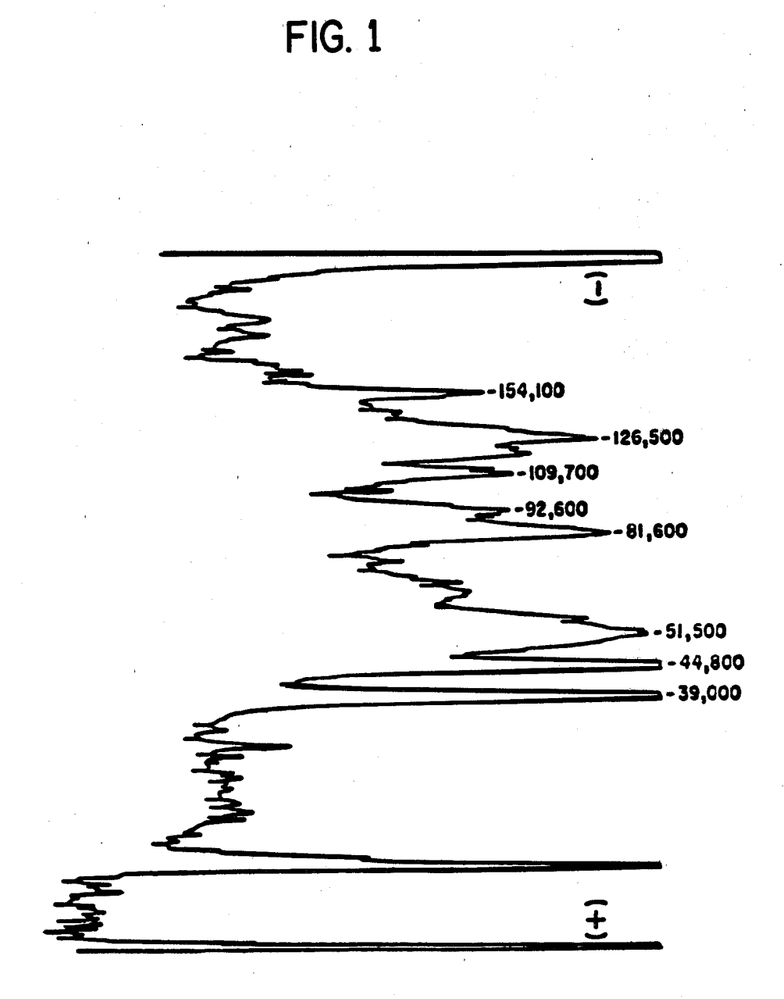
FIG. 1—Polypeptide composition of the HSV2 antigen isolated by *Lens culinaris* lectin-Sepharose affinity chromatography. Electrophoresis was done as described in Courtney, McCombs and Melnick, *Virology* 43, 356–365 (1971). Polypeptides were stained with Coomassie blue and the densitometer tracing was obtained by scanning the gel at a wave length of 540 nm. The numbers accompanying the peaks are molecular weights.
Figure 2:
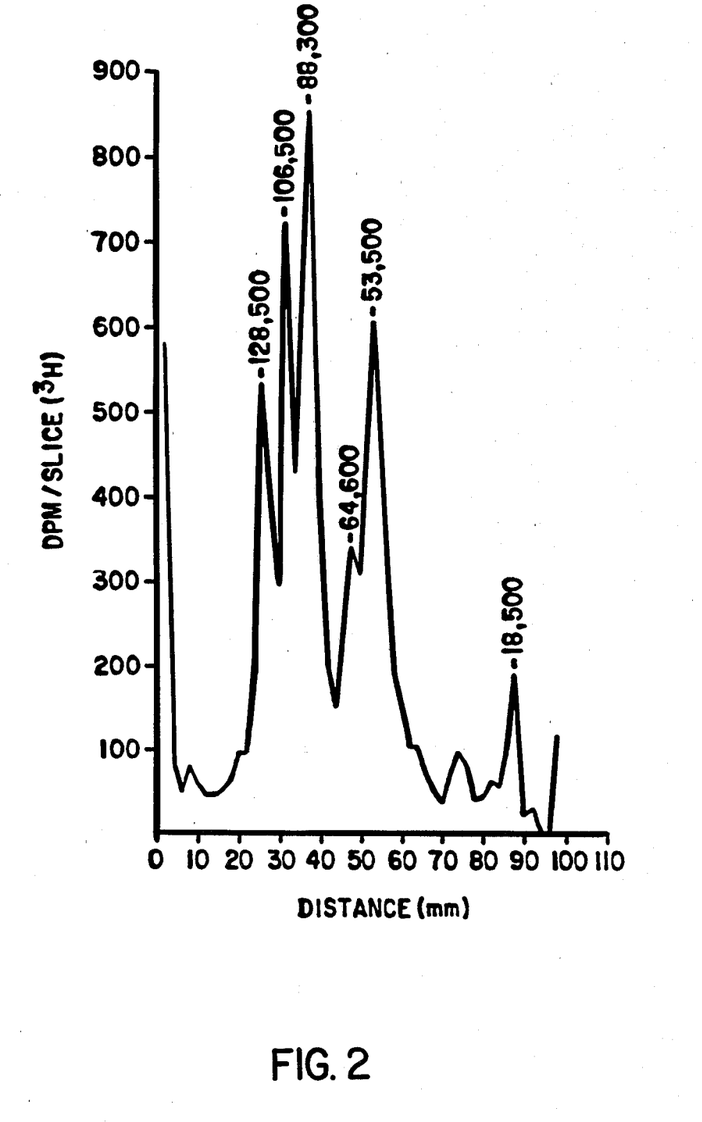
FIG. 2 Glycopolypeptide composition of the HSV2 antigen isolated by *Lens culinaris* lectin-Sepharose affinity chromatography. The viral glycoproteins were labeled in vitro by adding ($^3$H)glucosamine to the infected cells four hours after infection. Electrophoresis was performed as described in FIG. 1 and the radioactivity profile was obtained by slicing the gel into 2 mm segments, dissolving the polyacrylamide in 30% hydrogen peroxide and monitoring for radioactivity in a scintillation spectrometer.

The mixture is pumped onto the adsorbent column and the column subsequently washed with 5 column volumes of starting buffer. Then, the viral-directed glycoproteins are desorbed from the column with 5 column volumes of 0.2 M α-methyl-D-mannoside in starting buffer. The glycoprotein enriched fraction contains 6-major and 5–8 minor polypeptides as shown in FIG. 1 which include three groups of viral directed glycoproteins: about 110,000–130,000 daltons; about 83,000–90,000 daltons; and about 55,000–60,000 daltons as shown in FIG. 2. This fraction contains <50 ng of DNA and <100 ng of RNA per 100 μg protein. No intact or disrupted viruses or nucleocapsids are detected by electron microscopy and no live virus is isolated by tissue culture methods.

The glycoprotein fraction from the *Lens culinaris* lectin-Sepharose column is chromatographed on a small column of polymerized dextran, i.e., Sephadex G-50, to remove any lectin which may have leaked from the affinity adsorbents and the unadsorbed fraction is collected. This treatment is optional and may be omitted.

The unadsorbed HSV2 glycoprotein fraction is sterile filtered through a 0.2μ porosity Nuclepore filter and diluted to the protein use level with sterile pyrogen-free physiologically acceptable phosphate buffered saline. Optionally, formalin is added to a concentration of 100 μg/ml and the mixture incubated for 72 hours at 36° C. to further insure against the possibility of the presence of residual infectious HSV2 virus and to inactivate any residual single-stranded DNA.

For use as a vaccine, the HSV2 subunit antigen is adsorbed to alum and residual unbound Triton X-100 is removed by the following procedure. The antigen is adjusted to the desired protein use level, 40 μg per dose, and 10% $AlK(SO_4)_2.12H_2O$ (alum) is added to give a final alum concentration of 8.5 mg/ml. During the addition of alum, 1 N NaOH is used to maintain a pH of 5.2–6.0. After stirring at room temperature for 1 hour, the mixture is centrifuged for 10 minutes at 270×G. The supernatant is removed and the protein is measured (Lowry) in both the supernatant and the alum vaccine to determine the amount adsorbed. The alum is resuspended to a volume equal to the original antigen solution in sterile physiological saline (pyrogen-free) or in saline containing 1:20,000 thimerosal. The alum adsorbed vaccine may be washed once or twice with saline in order to reduce the Triton X-100 concentration in minimal amounts before resuspension. The alum adsorbed vaccine is stored at 4° C.

EXAMPLE 2

The process of Example 1 is repeated except that the infected cells are removed mechanically from the culture vessels and washed with phosphate buffered saline (PBS) i.e., 0.15 M NaCl, 0.0063 M sodium phosphate, pH 7.2. The washed cells are resuspended in pyrogen-free distilled water to give a cell concentration of approximately $1-2\times10^7$ cells/ml and are disrupted by flow sonication (3 cycles at 150 ml/min.) with a heat exchanger to maintain the temperature at about 4° C. The disrupted cells are centrifuged at 800 g for 20 minutes at 4° C. and the supernatant fluids are pooled. The supernatant fluid is adjusted to a final concentration of 2% Triton X-100, 1.0 M NaCl, 50 mM Tris-HCl, pH 7.5, 2 mM PMSF, 4.75% ethanol (to solubilize the PMSF), and a Lowry protein concentration of about 2 mg/ml. The mixture is suspended with a tissue homogenizer and incubated at 20°–23° C. for 1 hour with intermittant homogenization, and then centrifuged at 105,000 g for 1 hour at 20°–23° C. The supernatant fluid is collected and further processed as described in Example 1.

EXAMPLE 3

The processes of Example 1 and Example 2 are repeated except that DEAE-cellulose chromatography is substituted for *Lens culinarus* lectin affinity chromatography and Sephadex G-50 chromatography is omitted. The supernatant of the Triton X-100 extract is dialyzed against 1% Triton X-100, 10 mM Tris-HCl, pH 7.5 (starting buffer) at 4° C. The dialyzed extract is applied to a DEAE-cellulose column equilibrated in starting buffer and chromatographed at 4° C. After all the sample has entered the column, it is washed with the starting buffer to remove unadsorbed proteins and the adsorbed proteins are eluted with a 0–0.6 MNaCl gradient in starting buffer. The 25–200 mM NaCl fractions, which are richest in viral glycoproteins, are pooled. This pool is free of detectable double stranded DNA but contains about 1% single-stranded DNA or DNA fragments and 1-2% RNA. There are >30 polypeptides ranging in molecular weight from $\leq 17,000$ to $\geq 322,000$. The fraction also contains 3 groups of viral directed glycoproteins: about 110,000–130,000 daltons; about 83,000–90,000 daltons; and about 55,000–60,000 daltons. No intact or disrupted viruses or nucleocapsids are detected in the fraction by electron microscopy and no live virus is isolated by tissue culture methods.

EXAMPLE 4

Herpes simplex type 1 (HSV1) infected cells are prepared essentially as described in Example 1 except that HSV1 is used in lieu of HSV2. The infected cells are harvested and extracted essentially as described in Example 2 except that the low speed supernatant from the sonicated cells is centrifuged at 105,000 g for 1 hour at 4° C. to concentrate the virus, and the Triton X-100 extracting medium in which the pellet is resuspended contains 0.15 M NaCl instead of 1.0 M as employed for HSV2. The resulting extract is fractionated on the lectin concanavalin A as described below.

The affinity adsorbent, Con A-Sepharose (concanavalin A covalently linked to Sepharose), obtained from a commercial supplier, is suspended in 1% Triton X-100, 0.15 M NaCl, 50 mM Tris-HCl, pH 7.5 (starting buffer). It is placed into a 1.6 cm (inside diameter) chromatography column and allowed to settle to a height of 3.3 cm. The adsorbent is washed (20 ml/hr) with 20 ml of 0.2 M α-methyl-D-mannoside in starting buffer, followed by 2 M NaCl in starting buffer, and finally washed with four bed volumnes of starting buffer.

Figure 3:
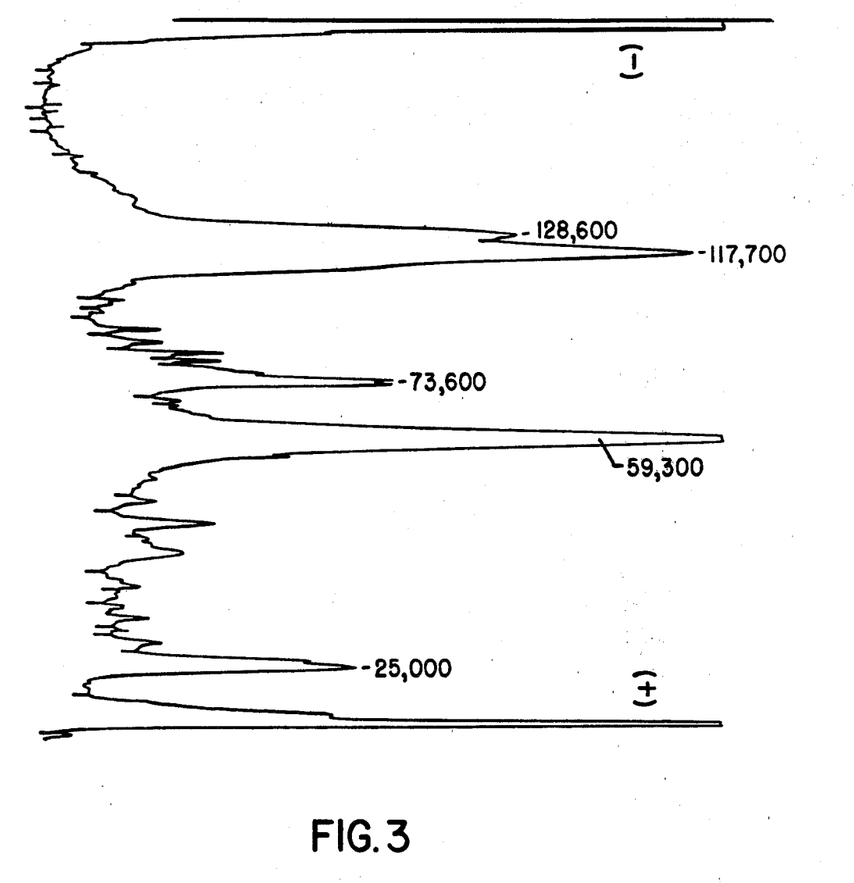
FIG. 3—Polypeptide composition of the HSV1 antigen isolated by con A-Sepharose affinity chromatography. Electrophorsis was done as described in FIG. 1.
Figure 4:
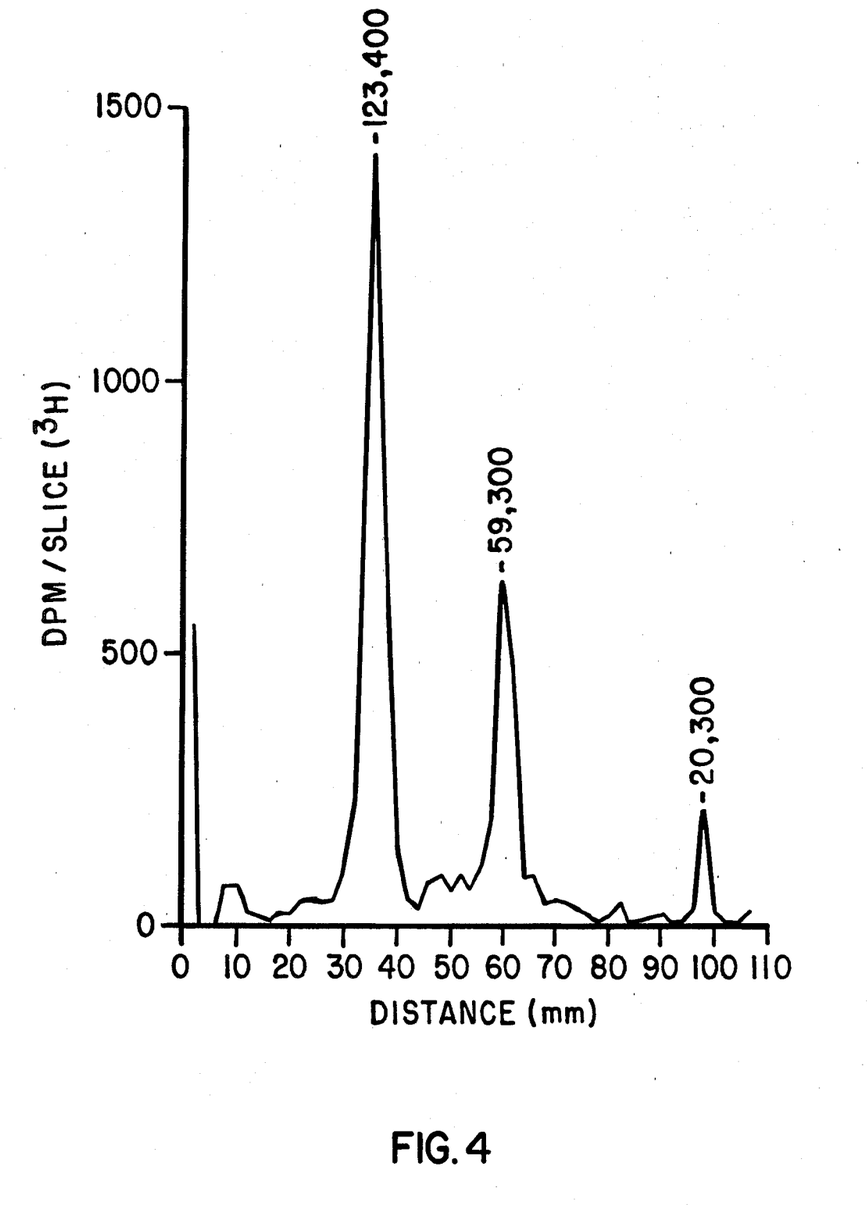
FIG. 4—Glycopolypeptide composition of the HSV1 antigen isolated by con A-Sepharose affinity chromatography. The analysis was done as described in FIG. 2.

The extract is pumped onto the adsorbent and the adsorbent is washed with 20 ml of the starting buffer. The glycoprotein fraction is eluted from the adsorbent with 30 ml of 0.2 M α-methyl-D-mannoside in starting buffer. The adsorbed fraction contains three major and six minor polypeptides as shown in FIG. 3, among which are the major viral-directed glycoproteins of 123,000 and 60,000 molecular weight as shown in FIG. 4. No intact or disrupted viruses or nucleocapsids are detected by electron microscopy and no live virus is isolated by tissue culture methods.

EXAMPLE 5

Three groups of guinea pigs (12 in each group) are injected intramuscularly at four week intervals with 1.0 ml doses containing varying amounts of the HSV2 subunit of the present invention adsorbed to alum adjuvant. The following table shows the dosage administered to each group at each injection and the number of animals out of the total in that group showing neutralizing antibody formation when tested on day 0, 28, 56 and 84.

| Group | Vaccine Dose (μg/ml) | No. of Animals Showing Neutralizing Antibody Response | | | |
|---|---|---|---|---|---|
| | | Day 0 | Day 28 | Day 56 | Day 84 |
| A | 10 | 0/12 | 9/12 | 12/12 | 12/12 |
| B | 1 | 0/12 | 1/10 | 6/10 | 10/10 |
| C | 0.1 | 0/12 | 0/12 | 0/12 | 3/11 |

Significantly, all of the guinea pigs show a neutralizing antibody response after two doses of vaccine at a dosage level of 10 μg and after 3 doses of vaccine at a dosage level of 1 μg.

EXAMPLE 6

Three groups of mice (20 in each group) are injected twice intraperitoneally at four week intervals with 0.5 ml doses containing varying amounts of the HSV2 subunit of the present invention adsorbed to alum adjuvant or with placebo vaccine. Two weeks after the last injection of vaccine, the animals are challenged with live HSV2 virus inoculated by the footpad route. The following table shows the dosage administered to each group at each injection of vaccine, the number of animals out of the total in that group that die after challenge, the mean survival time and the vaccine protective efficacy.

| Group | Vaccine Dose (μg/0.5 ml) | No. of Mice Dead After Challenge with HSV2 | | | | | Mean Survival Time (Days) | Protective Efficacy on Day 28 & (significance) |
|---|---|---|---|---|---|---|---|---|
| | | Day 0 | Day 7 | Day 14 | Day 21 | Day 28 | | |
| A | 40 | 0/20 | 0/20 | 2/20 | 5/20 | 7/20 | 26 | 62% (P = 0.0008) |
| B | 10 | 0/20 | 0/20 | 1/20 | 5/20 | 8/20 | 26 | 56% (P = 0.0022) |
| C(placebo) | 0 | 0/20 | 0/20 | 18/20 | 18/20 | 18/20 | 12 | — |

Significantly, more than 50% of the animals receiving two doses of vaccine at a dosage level of 10 or 40 μg are protected against death as compared to the placebo control animals. Additionals, the mean survival time is increased greater than two-fold.

EXAMPLE 7

Three groups of mice (20 in each group) are injected twice intraperitoneally at four week intervals with 0.5 ml doses containing varying amounts of the HSV2 subunit of the present invention adsorbed to alum adjuvant or with placebo vaccine. Two weeks after the last injection of vaccine, the animals are challenged with live HSV2 virus inoculated by the intracerebral route. The following table shows the dosage administered to each group at each injection of vaccine, the number of animals out of the total in that group that die after challenge, the mean survival time and the vaccine protective efficacy.

| Group | Vaccine Dose (μg/0.5 ml) | No. of Mice Dead After Challenge with HSV2 | | | | Mean Survival Time (Days) | Protective Efficacy on Day 21 & (significance) |
|---|---|---|---|---|---|---|---|
| | | Day 0 | Day 7 | Day 14 | Day 21 | | |
| A | 40 | 0/20 | 2/20 | 5/20 | 7/20 | 16 | 65% (P < 0.0001) |
| B | 10 | 0/20 | 5/20 | 10/20 | 11/20 | 13 | 45% (P = 0.0012) |
| C(placebo) | 0 | 0/20 | 10/20 | 17/20 | 20/20 | 8 | — |

Significantly, more than 50% of the animals receiving two doses of vaccine at a dosage level of 40 μg are protected against death as compared to the placebo control animals. Additionally, the mean survival time is increased two-fold. The administration of vaccine at a dosage level of 10 μg also exerts a beneficial effect but to a lesser degree.

EXAMPLE 8

Two groups of hairless (HRS) mice are injected twice intraperitoneally at four week intervals with 0.5 ml doses containing 20 μg of the HSV2 subunit of the present invention adsorbed to alum adjuvant or with placebo vaccine. Two weeks after the last injection of vaccine, the animals are challenged with live HSV1 virus inoculated by scarification of the facial area. The incidence of skin lesions at the site of challenge, mortality and latent trigeminal ganglionic infection are summarized in the following table.

|  | Response after HSV1 Challenge | | |
|---|---|---|---|
| Vaccine | Skin Lesions (Day 6) | Mortality (Day 21) | Latent Ganglionic Infection (Day 21-23) |
| HSV2 vaccine (20 μg/dose) | 4/19 | 0/19 | 1/19 |
| Placebo | 38/40 | 8/40 | 25/32 |

As compared to the control placebo vaccine, the HSV2 subunit vaccine significantly reduces the incidence of skin lesions ($P<0.0001$), mortality ($P=0.0009$) and latent ganglionic infection ($P<0.0001$) caused by challenge of the animals with the heterologous type 1 HSV.

EXAMPLE 9

Three groups of guinea pigs (12 in each group) are injected intramuscularly at four week intervals with 1.0 ml doses containing varying amounts of the HSV1 subunit of the present invention adsorbed to alum adjuvant. The following table shows the dosage administered to each group at each injection and the number of animals out of the total in that group showing neutralizing antibody formation when tested on day 0, 28, 56 and 84.

| Group | Vaccine Dose (μg/ml) | No. of Animals Showing Neutralizing Antibody Response | | | |
|---|---|---|---|---|---|
| | | Day 0 | Day 28 | Day 56 | Day 84 |
| A | 10 | 0/12 | 12/12 | 12/12 | 12/12 |
| B | 1 | 0/12 | 8/12 | 10/10* | 12/12 |
| C | 0.1 | 0/12 | 3/12 | 6/12 | 12/12 |

*2 animals not tested.

Significantly, all of the guinea pigs tested show a neutralizing antibody response after one dose of vaccine at a dosage level of 10 μg, after two doses of vaccine at a dosage level of 1 μg and after three doses of vaccine at a dosage level of 0.1 μg.

EXAMPLE 10

Phosphate buffered saline, 800 ml, containing 100 μg/ml of the product of Example 4 is stirred in a beaker. A volume of 10% alum, $AlK(SO_4)_2.12H_2O$, (68 ml) calculated to give an alum concentration of 8.5 mg/ml is added slowly while adding 1 N NaOH simultaneously (dropwise) to keep the pH of the suspension from dropping below pH 5.2. After addition of the alum has been completed, the suspension is adjusted to pH 6.8 with 10 N NaOH. The suspension is then stirred for 1-2 hours at room temperature. At the end of the stirring period, the suspension is transferred to appropriate centrifuge bottles and centrifuged for 10 minutes at $270\times G$. The suspension liquid is decanted and discarded. The pellet is resuspended in pyrogen-free physiological saline to a final volume equal to the initial volume of the antigen solution. The alum adsorbed vaccine may be washed once or twice with saline before resuspension in order to reduce the Triton X-100 concentration to minimal amounts.

What is claimed is:

1. An antigenic, immunogenic HSV-2 subunit vaccine consisting essentially of 3 groups of viral directed membrane-bound glycoproteins which are soluble in the presence of a non-ionic or anionic surfactant, the first of the three groups being from about 110,000 to about 130,000 daltons, the second of the three groups being from about 83,000 to about 90,000 daltons, and the third of the three groups being from about 55,000 to about 60,000 daltons, the subunit vaccine being substantially free of intact DNA and being capable of inducing neutralizing antibody and of being administered as a vaccine at a protein use level of from about 1 to about 100 μg.

2. A vaccine according to claim 1 additionally containing a stabilizer.

3. A vaccine according to claim 1 additionally containing an adjuvant.

4. An antigenic, immunogenic HSV-1 subunit vaccine consisting essentially of two groups of viral directed membrane-bound glycoproteins which are soluble in the presence of a nonionic or anionic surfactant, the first group being about 123,000 daltons and the second group being about 60,000 daltons, the subunit being substantially free of intact DNA and being capable of inducing neutralizing antibody and of being administered as a vaccine at a protein use level of from about 1 to about 100 μg.

5. A vaccine according to claim 4 additionally containing a stabilizer.

6. A vaccine according to claim 4 additionally containing an adjuvant.

7. A vaccine comprising an antigen according to claim 1 adsorbed on alum.

8. A vaccine comprising an antigen according to claim 4 adsorbed on alum.

* * * * *